(12) United States Patent
Tsukada

(10) Patent No.: US 9,202,134 B2
(45) Date of Patent: *Dec. 1, 2015

(54) LEAF AREA INDEX MEASUREMENT SYSTEM, DEVICE, METHOD, AND PROGRAM

(75) Inventor: Masato Tsukada, Minato-ku (JP)

(73) Assignee: NEC CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/824,555

(22) PCT Filed: Dec. 2, 2011

(86) PCT No.: PCT/JP2011/006763
§ 371 (c)(1),
(2), (4) Date: Mar. 18, 2013

(87) PCT Pub. No.: WO2012/073519
PCT Pub. Date: Jun. 7, 2012

(65) Prior Publication Data
US 2013/0182911 A1    Jul. 18, 2013

(30) Foreign Application Priority Data
Dec. 2, 2010  (JP) ................................ 2010-269718

(51) Int. Cl.
| G06K 9/00 | (2006.01) |
| G06K 9/60 | (2006.01) |
| A01G 7/00 | (2006.01) |
| G01B 11/28 | (2006.01) |
| G01N 21/84 | (2006.01) |
| G01N 21/25 | (2006.01) |

(52) U.S. Cl.
CPC .. *G06K 9/60* (2013.01); *A01G 7/00* (2013.01); *G01B 11/285* (2013.01); *G01N 21/251* (2013.01); *G01N 21/84* (2013.01); *G01N 2021/8466* (2013.01)

(58) Field of Classification Search
None
See application file for complete search history.

(56) References Cited

U.S. PATENT DOCUMENTS

| 2001/0028862 A1 | 10/2001 | Iwata et al. |
| 2009/0281733 A1* | 11/2009 | Yamamoto ........... H04N 5/2254 702/19 |
| 2010/0115830 A1* | 5/2010 | Dube ............................... 47/17 |

FOREIGN PATENT DOCUMENTS

| JP | 11-132850 A | 5/1999 |
| JP | 2002-40022 A | 2/2002 |

(Continued)

OTHER PUBLICATIONS

JP2005-052045 tcomputer generated translation Mar. 3, 2005 Boku et al.*

(Continued)

*Primary Examiner* — Nancy Bitar
(74) *Attorney, Agent, or Firm* — Sughrue Mion, PLLC

(57) ABSTRACT

A leaf area index measurement system includes: a reflector placed in a neighborhood of a measurement target plant; imaging means placed at a position where no obstacle is present between the imaging means and the reflector, and for capturing an image of the reflector and outputting the captured image; intensity calculation means for calculating an intensity of light reflected by the reflector, based on the captured image output from the imaging means; and leaf area index calculation means for calculating a leaf area index, based on the intensity of light calculated by the intensity calculation means.

8 Claims, 4 Drawing Sheets

(56) References Cited

FOREIGN PATENT DOCUMENTS

| JP | 2002-238056 A | 8/2002 |
|----|---------------|--------|
| JP | 2005-98937 A | 4/2005 |
| JP | 2006-101768 A | 4/2006 |
| JP | 2006-284596 A | 10/2006 |
| JP | 2007-171033 A | 7/2007 |

OTHER PUBLICATIONS

Imari Sato, "Illumination Distribution from Shadows", Journal of Information Processing Society of Japan: Computer Vision and Image Media, Dec. 2000, pp. 31-40, vol. 41, No. SIG 10 (CVIM 1).

Masatoshi Aoki et al., "Remote sensing of chlorophyll content of leaf. II. Effective spectral reflection characteristics for evaluations of chlorophyll content and leaf area index of plant community", Environment Control in Biology, 1986, pp. 33-39, vol. 24, No. 1.

Takeshi Oishi et al., "Superimposing Human Appearance onto MR system by Simultaneous Capturing Surfaces and Illumination Environment by omnidirectional camera", Meeting on Image Recognition and Understanding, Jul. 2009, 8 pgs.

International Search Report for PCT/JP2011/006763 dated Mar. 6, 2012.

Tan et al., "The Main Methods for Determining Leaf Area Index", vol. 33, No. 3,Forest Inventory and Planning, Jun. 2008, 4 pgs.

Zou et al., "Optical Methods for In Situ Measuring Leaf Area Index of Forest Canopy:A Review", Chinese Journal of Applied Ecology,vol. 21, No. 11, Nov. 2010, 9.

Communication dated Sep. 30, 2014, issued by the State Intellectual Property Office of People's Republic of China, in counterpart Application No. 201180057911.2.

Ming et al., "Extraction of leaf area index of wheat based on image processing technique", vol. 33, No. 3, Jan. 2010, 6 pgs., with Communication dated Sep. 30, 2014, issued by the State Intellectual Property Office of People's Republic of China, in counterpart Application No. 201180057911.2.

Ling et al., "Leaf Area Index Estimation for Qinghai Spruce Forest Using Digital" vol. 24, No. 7, 2009, 6 pgs., with Communication dated Sep. 30, 2014, issued by the State Intellectual Property Office of People's Republic of China, in counterpart Application No. 201180057911.2

Communication dated Oct. 6, 2015 from the Japanese Patent Office in counterpart application No. 2012-546707.

* cited by examiner

LEAF AREA INDEX MEASUREMENT SYSTEM, DEVICE, METHOD, AND PROGRAM

CROSS REFERENCE TO RELATED APPLICATIONS

This application is a National Stage of International Application No. PCT/JP2011/006763 filed Dec. 2, 2011, claiming priority based on Japanese Patent Application No. 2010-269718 filed Dec. 2, 2010, the contents of all of which are incorporated herein by reference in their entirety.

TECHNICAL FIELD

The present invention relates to a leaf area index measurement system, a leaf area index measurement device, a leaf area index measurement method, and a leaf area index measurement program for measuring a leaf area index.

BACKGROUND ART

A leaf area index (hereafter "LAI") represents a total area of leaves overlapping in a direction (e.g. a vertical direction) per unit area in, for example, a plant community in agricultural land or forests. The LAI is used as one index for understanding plant growth or cultivation states.

As an LAI measurement method, a method of indirectly measuring the LAI using an illuminometer is proposed as an example. In this method, for instance, illuminance is measured above and below in a plant community, and the LAI is estimated based on the measured illuminance.

As a technique related to this, for instance, an LAI indirect measurement method is described in Patent Literature (PTL) 1.

In the method described in PTL 1, an indirect measurement system captures an image of a predetermined area for each of near-infrared light and red light, using a wide angle lens and an electronic imaging element. Next, the indirect measurement system obtains a luminance value for each of near-infrared light and red light, in each subdivision area formed by dividing the predetermined area. The indirect measurement system then calculates a luminance value ratio of near-infrared light and red light for each subdivision area, estimates a relative amount of solar radiation based on the luminance value ratio, and calculates the LAI from the relative amount of solar radiation.

CITATION LIST

Patent Literature(s)

PTL 1: Japanese Patent Application Laid-Open No. 2007-171033

SUMMARY OF INVENTION

Technical Problem

However, in the case of indirectly measuring the LAI using the illuminometer, an expensive illuminometer is necessary and also the measurement needs to be performed a plurality of times while moving the illuminometer, in order to determine the LAI in each of a plurality of locations in a community structure. Thus, a great deal of labor and cost are required.

The method described in PTL 1 achieves a certain degree of cost reduction by using the electronic imaging element in the indirect measurement system instead of the illuminometer. However, since sunlight is used, it is impossible to freely control an irradiation direction of light from the light source, posing a limit to directions in which the relative amount of solar radiation can be measured. Thus, locations or directions in which the LAI can be measured are limited in the case of using the method described in PTL 1.

In view of this, the present invention has an object of providing a leaf area index measurement system, a leaf area index measurement device, a leaf area index measurement method, and a leaf area index measurement program capable of automatically measuring a leaf area index easily at low cost, without a limit to measurement locations or directions.

Solution to Problem

A leaf area index measurement system according to the present invention includes: a reflector placed in a neighborhood of a measurement target plant; imaging means placed at a position where no obstacle is present between the imaging means and the reflector, and for capturing an image of the reflector and outputting the captured image; intensity calculation means for calculating an intensity of light reflected by the reflector, based on the captured image output from the imaging means; and leaf area index calculation means for calculating a leaf area index, based on the intensity of light calculated by the intensity calculation means.

A leaf area index measurement device according to the present invention is a leaf area index measurement device for measuring a leaf area index in a leaf area index measurement system that includes: a reflector placed in a neighborhood of a measurement target plant; and imaging means placed at a position where no obstacle is present between the imaging means and the reflector, and for capturing an image of the reflector and outputting the captured image, the leaf area index measurement device including: intensity calculation means for calculating an intensity of light reflected by the reflector, based on the captured image output from the imaging means; and leaf area index calculation means for calculating the leaf area index, based on the intensity of light calculated by the intensity calculation means.

A leaf area index measurement method according to the present invention includes: providing a reflector in a neighborhood of a measurement target plant; providing imaging means placed at a position where no obstacle is present between the imaging means and the reflector, and for capturing an image of the reflector and outputting the captured image; calculating an intensity of light reflected by the reflector, based on the captured image output from the imaging means; and calculating a leaf area index, based on the calculated intensity of light.

A leaf area index measurement program according to the present invention is a leaf area index measurement program for measuring a leaf area index in a leaf area index measurement system that includes: a reflector placed in a neighborhood of a measurement target plant; and imaging means placed at a position where no obstacle is present between the imaging means and the reflector, and for capturing an image of the reflector and outputting the captured image, the leaf area index measurement program causing a computer to execute: an intensity calculation process of calculating an intensity of light reflected by the reflector, based on the captured image output from the imaging means; and a leaf area index calculation process of calculating the leaf area index, based on the calculated intensity of light.

Advantageous Effects of Invention

According to the present invention, it is possible to automatically measure a leaf area index easily at low cost, without a limit to measurement locations or directions.

DESCRIPTION OF EMBODIMENT(S)

Figure 1:
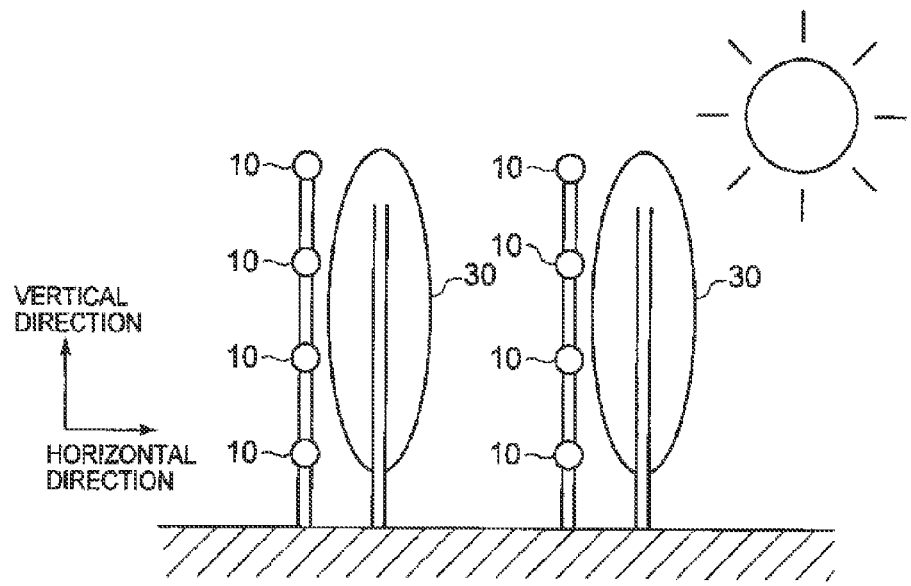
FIG. 1 is a front view of a measurement system using an LAI measurement system according to the present invention, as seen from front with respect to a plant community.
Figure 2:
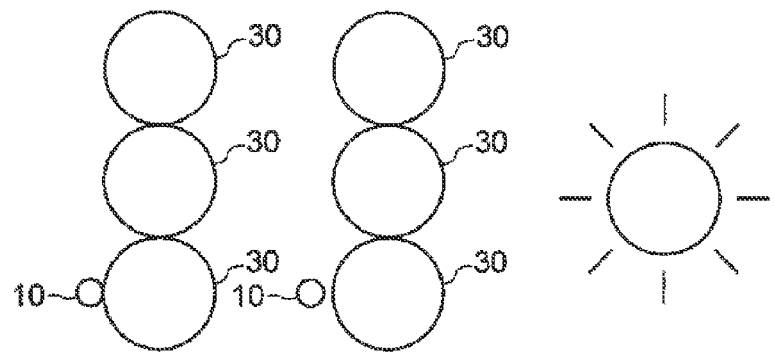
FIG. 2 is a top view of the measurement system using the LAI measurement system, as seen from top with respect to the plant community.
Figure 2:

An embodiment of the present invention is described below, with reference to drawings. FIG. 1 is a front view of a measurement system using an LAI measurement system (leaf area index measurement system) according to the present invention, as seen from front with respect to a plant community. FIG. 2 is a top view of the measurement system using the LAI measurement system, as seen from top with respect to the plant community. In this exemplary embodiment, it is assumed that a plant community 30 is a plant group in which plants for agricultural crops are arranged in line, as shown in FIG. 1. Though FIG. 1 shows a sectional view taken along a section of the plant community 30, the plant community 30 is a plant group in which plants are arranged in line in a depth direction (a direction from front to back of the plant community 30 as seen in FIG. 1, hereafter also referred to as "longitudinal direction") as shown in FIG. 2.

In this exemplary embodiment, the expressions such as "vertical direction" and "horizontal direction" are used, too. The "vertical direction" represents a direction vertical to the ground, and the "horizontal direction" represents a direction horizontal to the ground, as shown in FIG. 1.

Though this exemplary embodiment describes, as an example, the case where the LAI measurement system is applied to measurement of an LAI in a plant community for agricultural crops (e.g. tomatoes, cucumbers) in agricultural land such as a field or a plastic greenhouse, the present invention is not limited to the example in this exemplary embodiment. The LAI measurement system may be applied to, for instance, measurement of an LAI in a tree group in forests.

As shown in FIGS. 1 and 2, an array group in which a plurality of reflectors 10 are arranged in the vertical direction is installed in a neighborhood of the plant community 30. Moreover, as shown in FIG. 2, a camera 20 is installed at a position where an image of the reflectors 10 can be captured without being obstructed by the plant community 30 (in this example, the camera 20 is placed on the front side as shown in FIG. 2, i.e. the camera 20 is placed so that no obstacle such as leaves obstructing the reflectors 10 is present between each reflector 10 and the camera 20).

The reflectors 10 are each specifically realized by a spherical body whose surface has a Lambert reflection characteristic and color information is known. Though eight reflectors 10 are arranged in the vertical direction in the example shown in FIG. 1 (four reflectors 10 are arranged in the vertical direction per plant community 30 as shown in FIG. 1), the number of reflectors 10 that can be arranged is not limited to the example in this exemplary embodiment. For instance, ten or more reflectors 10 may be arranged (five or more reflectors 10 may be arranged in the vertical direction per plant community 30).

The reflectors 10 are at least reflectors that do not specularly reflect light. For example, as long as the reflectors 10 diffusely reflect light, the reflectors 10 may perfectly diffusely reflect light or imperfectly diffusely reflect light. In this exemplary embodiment, the case where the reflectors 10 are red spherical bodies is used as an example. However, the present invention is not limited to the example in this exemplary embodiment, and the reflectors 10 may be, for instance, any of various polyhedral structures or flat reflector plates. Besides, the color of the reflectors 10 is not limited to red. As long as the color is known, the color may be white, gray, yellow, or orange. It is, however, preferable that the color of the reflectors 10 is at least other than green so as to be distinguishable from the plants in the plant community 30.

Since the reflectors 10 are arranged in the neighborhood of the plant community 30, the reflector 10 positioned top is highest in the intensity of reflected light and the intensity of reflected light decreases in the downward direction of the reflectors 10, due to shadows of the plant community 30 and the like. Accordingly, by measuring the intensities of light reflected from the plurality of reflectors 10 arranged in the vertical direction and comparing the measured intensities with each other, the LAI in the vertical direction can be measured, and the degree of leaf overlap in the plant community 30 as seen in the vertical direction can be recognized. Note that the neighborhood of the plant community 30 is within a predetermined distance (e.g. within 50 cm) from the plant community 30. When arranging the reflectors 10 in the vertical direction, the reflectors 10 are arranged so that there are appropriate differences in the intensity of reflected light between the reflectors 10.

The camera 20 is specifically realized by an imaging device such as a digital camera capable of capturing color images. The camera 20 is not limited to a camera for capturing still images and may be realized, for example, by a video camera capable of capturing moving images, as long as it is capable of capturing color images. The camera 20 has a function of capturing the image of the reflectors 10 and outputting the captured image to a below-mentioned LAI measurement device 40 (not shown in FIGS. 1 and 2).

In this exemplary embodiment, it is desirable to place the camera 20 at such a position that enables image capture of upper hemispheres of the reflectors 10 which are spherical bodies (e.g. a position higher than all reflectors in the vertical direction), in order to capture the image of the reflectors 10 irradiated with sunlight and measure the LAI in the vertical direction.

Though FIG. 1 shows the case where four reflectors 10 are arranged in the vertical direction in one location in the neighborhood of the plant community 30 to perform the measurement, an array of four reflectors 10 in the vertical direction may equally be placed at predetermined intervals (e.g. intervals of 50 cm) in the longitudinal direction of the plant community 30 (i.e. reflectors are arranged in a lattice when seen from a longitudinal side) to perform the measurement. In this way, an LAI distribution in the longitudinal direction of the plant community 30 can be measured, too.

Figure 3:
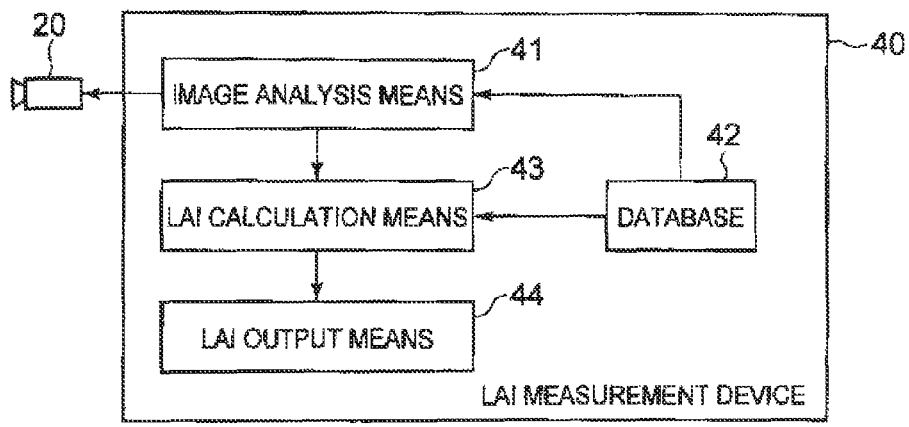
FIG. 3 is a block diagram showing an example of a structure of the LAI measurement system.

FIG. 3 is a block diagram showing an example of a structure of the LAI measurement system. As shown in FIG. 3, the LAI measurement system includes the LAI measurement device 40, in addition to the camera 20 for capturing the image of the reflectors 10 shown in FIG. 2. The captured image is output from the camera 20 to the LAI measurement device 40, as shown in FIG. 3. The LAI measurement device 40 is specifically realized by an information processing device such as a personal computer operating according to a program. As shown in FIG. 3, the LAI measurement device 40 includes image analysis means 41, a database 42, LAI calculation means 43, and LAI output means 44.

The image analysis means 41 is specifically realized by a CPU of the information processing device operating according to the program. The image analysis means 41 has a function of calculating a luminance value of the captured image received from the camera 20.

For example, based on the known color information and shape information of the reflector 10, the image analysis means 41 specifies, in the captured image, an area in which the reflector 10 is shown, and calculates a luminance value of the specified area. In this exemplary embodiment, the image analysis means 41 specifies an area in which a red object is shown in the captured image, and extracts a partial image of the specified area. In this exemplary embodiment, since the plurality of red reflectors 10 are arranged, the image analysis means 41 specifies a plurality of areas and extracts a partial image of each of the specified areas. The image analysis means 41 then calculates a luminance value of each extracted partial image.

The image analysis means 41 also has a function of transforming the calculated luminance value to illuminance. In this exemplary embodiment, the image analysis means 41 calculates the illuminance by extracting, from an illuminance transformation table stored in the below-mentioned database 42, the illuminance corresponding to the luminance value calculated by the image analysis means 41.

Alternatively, the image analysis means 41 may calculate the illuminance without using the illuminance transformation table stored in the database 42. The following describes an example of the illuminance calculation method. A method of calculating, through the use of the color information of the object (reflector 10) in the color image captured by the color image input device (camera 20) and the surface reflection characteristic of the object, illuminance at each position of the surface of the object in a luminous environment when capturing the color image is described below.

First, the image analysis means 41 obtains color information of the area of the object automatically detected using the color information and shape information of the input image. The image analysis means 41 then obtains RGB color information of the area of the object, and calculates XYZ tristimulus values based on the obtained RGB color information.

It is hereafter assumed that, regarding RGB captured by the color image input device, chromaticity of RGB phosphors and chromaticity of white color are designated beforehand as color characteristics of the color image input device, and the RGB data and the XYZ tristimulus values are in linear relationship.

In this case, the relationship between the RGB of the input image and the XYZ tristimulus values is expressed by the following Equation (1).

[Math. 1]

$$\begin{pmatrix} X \\ Y \\ Z \end{pmatrix} = RX \begin{pmatrix} R \\ G \\ B \end{pmatrix}$$ Equation (1)

Here, RX is a 3×3 transformation matrix.

The image analysis means 41 can transform the Y tristimulus value to absolute luminance Y (cd/m$^2$), by acquiring information of an aperture value F of a camera lens, a shutter speed, and a gain at image capture.

Next, the image analysis means 41 calculates apparent irradiance in each pixel position of the reflector in the image. The method described in Document 1 or the method described in Document 2 is applicable to the irradiance calculation.

Document 1: Imari Sato, Yoichi Sato, Katsushi Ikeuchi, "Illumination Distribution from Shadows", Journal of Information Processing Society of Japan: Computer Vision and Image Media, Vol. 41, No. SIG 10 (CVIM 1), December 2000

Document 2: Oishi, Okura, et al., "Superimposing Human Appearance onto MR system by Simultaneous Capturing Surfaces and Illumination Environment by omnidirectional camera", Meeting on Image Recognition and Understanding (MIRU2009), July 2009

Figure 6:
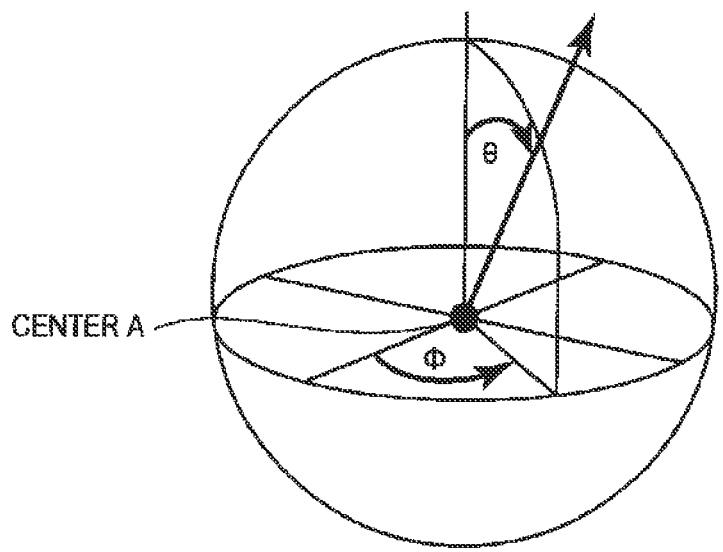
FIG. 6 is an explanatory diagram showing an example of a whole circumference light environment model taking a surface light source into account.

The following description uses a whole circumference light environment model taking a surface light source into account, with reference to FIG. 6. In this model, a radiance distribution of the light source from the whole circumference is observed on an assumption that an arbitrary point on the reflector is at a center A of the sphere and there is no obstacle between the light source and the center A. Let L(θ, φ) be the radiance distribution, where θ denotes an azimuth angle and φ denotes a zenith angle.

Illuminance E at the center A is an integral of incident light energy received from a small solid angle $d\omega_i$ which is expressed by a small azimuth angle $d\theta_i$ and a small zenith angle $d\phi_i$, in all directions.

[Math. 2]

$$E_A = \int_{-\pi}^{\pi} \int_0^{\frac{\pi}{2}} L_i(\theta_i, \varphi_i) \cos\theta_i \sin\theta_i \, d\theta_i \, d\varphi_i$$ Equation (2)

Here, $d\theta_i$ denotes the small azimuth angle, and $d\phi_i$ denotes the small zenith angle.

The precondition here is that there is no obstacle between the light source and the center A. Moreover, the light reflection characteristic of the reflector is Lambert reflection. Therefore, the light reflected at the center A is in a form of integrating ambient light incident on the center A from all directions. Thus, whether or not there is an obstacle between the light source and the center A is negligible, and the light reflected at the center A is constant regardless of a visual point direction.

Moreover, if a surface reflectance $S_A$ (color) of the reflector at the center A is known, a luminance value $I_A$ in the reflector recorded as the image is expressed by a product of the illuminance $E_A$ and the surface reflectance $S_A$ of the reflector. The luminance value $I_A$ is expressed using the Y tristimulus value calculated according to Equation (1).

[Math. 3]

$$I_A = \int_{-\pi}^{\pi} \int_{0}^{\frac{\pi}{2}} S_A L_i(\theta_i, \varphi_i) \cos\theta_i \sin\theta_i \, d\theta_i \, d\varphi_i = S_A E_A \quad \text{Equation (3)}$$

The image luminance reflects the spectral sensitivity characteristic of the camera expressed as a function of a wavelength λ. Suppose the spectral sensitivity characteristic of the camera is approximated by a delta function. Then, the wavelength λ can be regarded as a constant. Hence, the image luminance $I_A^k$ (k is r, g, b) at the point A is expressed as follows.

$$I_A^k = \tau^k S_A^k E_A^k \quad \text{Equation (4)}$$

Here, $\tau^k$ is the camera gain. Thus, the illuminance $E_A^k$ at the point A is calculated from the image luminance and the camera gain at the point A, according to Equation (4). Furthermore, if the geometric positional relationship between the reflector and the camera and the shape of the reflector are known, a normal vector at an arbitrary point on the surface of the reflector observable from the camera can be calculated through the use of simple geometry. That is, the illuminance calculated according to Equation (4) at the arbitrary point A on the surface of the reflector observable from the camera can be regarded as illuminance of a light source from the direction of the normal vector at the point A. It is therefore possible to calculate illuminance of a light source from a normal vector direction at all points on the surface of the reflector observable from the camera. This means illuminance can be calculated not only for light in the vertical direction but also for light leaking from an oblique direction or the horizontal direction.

The database 42 is specifically realized by a storage device such as a magnetic disk device or an optical disk device. In this exemplary embodiment, the database 42 stores the illuminance transformation table for transforming the luminance value to the illuminance. In detail, the illuminance transformation table stored in the database 42 includes the luminance value and the illuminance in association with each other. For example, the illuminance transformation table stored in the database 42 is created by, under several conditions as samples, setting illuminance measured using a commonly used illuminometer and a luminance value obtained from a captured image beforehand.

The database 42 also stores an LAI transformation table for transforming the illuminance to the LAI. In detail, the LAI transformation table stored in the database 42 includes the illuminance and the LAI in association with each other. For example, the LAI transformation table stored in the database 42 is created by, under several conditions as samples, setting illuminance measured using a commonly used illuminometer and an LAI calculated at the time beforehand.

The LAI calculation means 43 is specifically realized by the CPU of the information processing device operating according to the program. The LAI calculation means 43 has a function of calculating the LAI based on the illuminance calculated by the image analysis means 41. In detail, the LAI calculation means 43 calculates the LAI by extracting, from the LAI transformation table stored in the database 42, the LAI corresponding to a difference value of the illuminance calculated by the image analysis means 41.

The LAI output means 44 is specifically realized by the CPU of the information processing device operating according to the program and a display device such as a display. The LAI output means 44 has a function of outputting the LAI calculated by the LAI calculation means 43. For example, the LAI output means 44 displays the LAI calculated by the LAI calculation means 43, on the display device such as the display. The method of outputting the LAI is not limited to the method shown in this exemplary embodiment. As an example, the LAI output means 44 may output a file including the LAI calculated by the LAI calculation means 43. As another example, the LAI output means 44 may transmit the LAI calculated by the LAI calculation means 43, to another terminal via a network such as a LAN.

In this exemplary embodiment, the storage device of the LAI measurement device 40 stores various programs for measuring the LAI. For instance, the storage device of the LAI measurement device 40 stores an LAI (leaf area index) measurement program for causing a computer to execute: a process of calculating an intensity of light reflected by the reflector 10 based on a captured image output from imaging means; and a process of calculating a leaf area index based on the calculated intensity of light.

Figure 4:
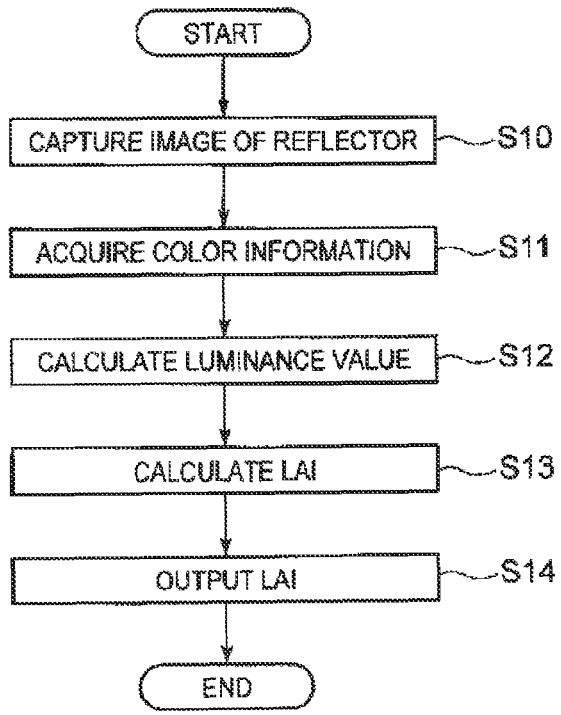
FIG. 4 is a flowchart showing an example of an operation of measuring an LAI using the LAI measurement system.

The following describes an operation of the LAI measurement system. FIG. 4 is a flowchart showing an example of an operation of measuring the LAI using the LAI measurement system. In this exemplary embodiment, the measurement is performed in a state where the array group in which the plurality of reflectors 10 are arranged in the vertical direction is positioned opposite to the side of the plant community 30 on which sunlight is currently incident, as shown in FIGS. 1 and 2. Moreover, the camera 20 is capable of capturing the image of the reflectors 10 without being obstructed by the plant community 30, and is installed at a higher position than all reflectors 10 in order to measure the LAI in the vertical direction.

First, the camera 20 captures the direction in which the reflectors 10 are arranged (step S10). The LAI measurement device 40 receives the captured image from the camera 20.

Next, the LAI measurement device 40 acquires, for example, the color information (red in this example) of the reflectors 10 stored in the storage device (not shown) beforehand (step S11), specifies the area in which the red object is shown in the captured image received from the camera 20, and extracts the partial image of the specified area. In this exemplary embodiment, since the plurality of red reflectors 10 are arranged, the image analysis means 41 specifies the plurality of areas, and extracts the partial image of each specified area. The LAI measurement device 40 then calculates the luminance value of each extracted partial image (step S12).

The LAI measurement device 40 transforms the calculated luminance value to the illuminance. In this exemplary embodiment, the LAI measurement device 40 extracts the illuminance corresponding to the calculated luminance value, from the illuminance transformation table stored in the database 42. Alternatively, the LAI measurement device 40 may calculate the illuminance in each pixel of the partial image of the area in which the reflector 10 is shown in the captured image as expressed by the above-mentioned Equation (4), based on the color information and the surface reflection characteristic.

The LAI measurement device 40 then calculates the LAI of the location where the reflector 10 is placed, based on the obtained illuminance (step S13). In this exemplary embodiment, the LAI measurement device 40 calculates the LAI, by extracting the LAI corresponding to the illuminance from the LAI transformation table stored in the database 42.

Thus, by using the spherical reflectors 10 having the Lambert reflection characteristic, the LAI measurement device 40 can calculate the LAI in the vertical direction at the location where the reflectors 10 are installed. Since the reflectors 10 are spherical, the LAI measurement device 40 can also calculate the LAI in an arbitrary direction other than the vertical direction by focusing on a specific part of the area in which the reflectors 10 are shown in the captured image.

Though this exemplary embodiment describes the case of calculating the LAI using the LAI transformation table in which the illuminance and the LAI are associated with each other beforehand, the LAI calculation method is not limited to the method shown in this exemplary embodiment. For example, the LAI measurement device 40 may calculate the LAI based on the calculated luminance value, without transforming the luminance value of the captured image to the illuminance. In such a case, for example, a table in which the luminance value and the LAI are associated with each other may be prepared beforehand so that the LAI measurement device 40 calculates the LAI by extracting the LAI corresponding to the calculated luminance value from the table.

As an alternative, for example, the LAI measurement device 40 may calculate the LAI by performing an operation using Equation (5) shown below.

$$I/I_0 = e^{-KF} \quad \text{Equation (5)}$$

In Equation (5), I denotes the intensity of light (which is specifically illuminance, but may also be a luminance value or the like) reflected by a reflector 10 out of the plurality of reflectors 10 placed in the neighborhood of the plant community 30. $I_0$ denotes the intensity of light (which is specifically illuminance, but may also be a luminance value or the like) reflected by a reference reflector 10 (in this example, the position of the reflector 10 attached at the top, which is usable as a reference light intensity because there is almost no influence of shadows of leaves and the like between the reflector 10 and the sun) out of the plurality of reflectors 10 placed in the neighborhood of the plant community 30. K denotes an absorption coefficient, which varies depending on plant and, even for the same plant, varies depending on external factors such as weather and time. F is an integral leaf area index.

In the case where the LAI measurement is completed for all reflectors 10, the LAI measurement device 40 displays the measured LAI on the display device such as the display (step S14). Here, the LAI measurement device 40 may display the LAI measured at each measurement point. Besides, for example in the case where the reflector group is arranged at predetermined intervals in the depth direction (longitudinal direction) and the measurement is performed on such reflectors 10 arranged in a lattice, the LAI measurement device 40 may display a graph showing LAI changes with the depth direction as the horizontal axis. Thus, the LAI measurement value can be displayed by various display methods. In addition, the LAI measurement device 40 may, for example, output a file including the measured LAI, or transmit the LAI to another terminal via a network.

As described above, in this exemplary embodiment, the LAI measurement device 40 measures the LAI based on the captured image from the camera 20, without using an expensive illuminometer. Moreover, the LAI measurement device 40 performs the LAI measurement not by measuring sunlight as a direct light source but by measuring light reflected from the reflectors 10 placed in the neighborhood of the plant community 30. This enables the LAI measurement device 40 to automatically measure the LAI (leaf area index) easily at low cost, without a limit to measurement locations or directions.

Further, the LAI measurement may be performed in a state where the reflectors 10 arranged in line in the vertical direction are provided at predetermined intervals (e.g. 50 cm) in the depth direction of the plant community 30. In this way, the LAI measurement device 40 can easily measure the LAI distribution in the depth direction (longitudinal direction) of the plant community 30, at reduced cost.

In terms of reducing labor in measurement work, a structure in which a plurality of illuminometers are arranged in the vertical direction or the depth direction to measure the LAI might be suggested. However, such a structure requires the use of many expensive illuminometers, which leads to an increase in cost. In this exemplary embodiment, on the other hand, the LAI measurement device 40 is capable of measuring the LAI in the vertical direction or the depth direction all at once simply by processing the image captured by the camera 20, without using an expensive illuminometer. Thus, the LAI measurement device 40 can achieve both a reduction in cost and a reduction in workload for LAI measurement.

If an illuminometer is placed outdoors such as in agricultural land or forests, the illuminometer tends to be stained. This requires workload for maintenance, and increases a possibility of troubles. In this exemplary embodiment, on the other hand, the LAI measurement device 40 can easily perform the measurement merely by arranging many reflectors 10. Hence, any workload for maintenance or troubles can be prevented.

Figure 5:
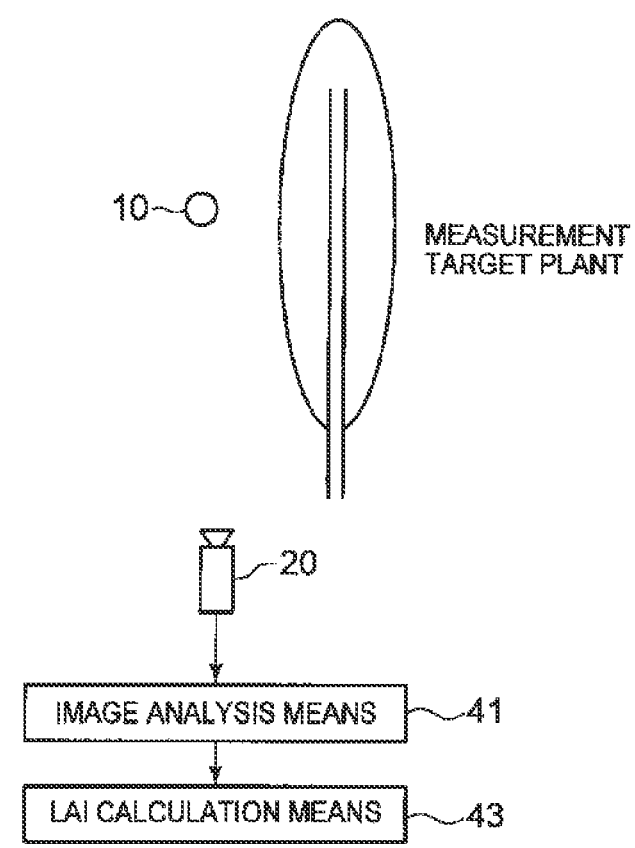
FIG. 5 is a block diagram showing an example of a minimum structure of the LAI measurement system.

The following describes a minimum structure of the LAI (leaf area index) measurement system according to the present invention. FIG. 5 is a block diagram showing an example of the minimum structure of the LAI measurement system. As shown in FIG. 5, the LAI measurement system includes a reflector 10, a camera 20, image analysis means 41, and LAI calculation means 43.

The reflector 10 is placed on a side of a measurement target plant opposite to the sun. The camera 20 has a function of capturing an image of the reflector 10 and outputting the captured image. The image analysis means 41 calculates an intensity of light (e.g. illuminance, luminance value) reflected by the reflector 10, based on the captured image output from the camera 20. The LAI calculation means 43 has a function of calculating an LAI (leaf area index) based on the intensity of light calculated by the image analysis means 41.

The LAI measurement system having the minimum structure shown in FIG. 5 is capable of automatically measuring a leaf area index easily at low cost, without a limit to measurement locations or directions.

Note that the exemplary embodiment describes above shows characteristic structures of an LAI (leaf area index) measurement system as in the following (1) to (5).

(1) A leaf area index measurement system includes: a reflector (e.g. the reflector 10) placed in a neighborhood of a measurement target plant; imaging means (e.g. the camera 20) placed at a position where no obstacle is present between the imaging means and the reflector, and for capturing an image of the reflector and outputting the captured image; intensity calculation means (e.g. realized by the image analysis means 41) for calculating an intensity of light (e.g. illuminance, luminance value) reflected by the reflector, based on the captured image output from the imaging means; and leaf area index calculation means (e.g. realized by the LAI calculation means 43) for calculating a leaf area index, based on the intensity of light calculated by the intensity calculation means.

(2) In the leaf area index measurement system, the intensity calculation means may calculate a luminance value of the reflector in the captured image, as the intensity of light, wherein the leaf area index calculation means calculates the leaf area index, based on the luminance value calculated by the intensity calculation means as the intensity of light.

(3) In the leaf area index measurement system, the intensity calculation means may calculate illuminance based on a luminance value of the reflector in the captured image, as the intensity of light, wherein the leaf area index calculation means calculates the leaf area index, based on the illuminance calculated by the intensity calculation means as the intensity of light.

(4) The leaf area index measurement system may include storage means (e.g. the database 42) for storing the leaf area index in association with the intensity of light, wherein the leaf area index calculation means calculates the leaf area index by extracting, from the storage means, the leaf area index corresponding to the intensity of light calculated by the intensity calculation means.

(5) In the leaf area index measurement system, the reflector may be provided with a predetermined color, wherein the intensity calculation means specifies, in the captured image, an area in which an object provided with the predetermined color is shown, and calculates an intensity of light of the specified area.

Though the present invention has been described with reference to the above exemplary embodiment and examples, the present invention is not limited to the above exemplary embodiment and examples. Various changes understandable by those skilled in the art within the scope of the present invention can be made to the structures and details of the present invention.

This application claims priority based on Japanese Patent Application No. 2010-269718 filed on Dec. 2, 2010, the disclosure of which is incorporated herein in its entirety.

INDUSTRIAL APPLICABILITY

The present invention is applicable to measurement of an LAI (leaf area index) in a plant community in agricultural land or forests.

REFERENCE SIGNS LIST

10 reflector
20 camera
30 plant community
40 LAI measurement device
41 image analysis means
42 database
43 LAI calculation means
44 LAI output means

The invention claimed is:

1. A leaf area index measurement system comprising:
a plurality of reflectors placed in a neighborhood of a measurement target plant; and
a processor configured to execute:
an imaging unit placed at a position where no obstacle is present between the imaging unit and the reflectors, and for capturing images of the reflectors and outputting the captured images;
an intensity calculation unit for calculating an intensity of light reflected by each of the reflectors, based on the captured images output from the imaging unit; and
a leaf area index calculation unit for calculating a leaf area index, based on the intensity of light calculated by the intensity calculation unit.

2. The leaf area index measurement system according to claim 1, wherein the intensity calculation unit calculates a luminance value of each of the reflectors in the captured images, as the intensity of light, and
wherein the leaf area index calculation unit calculates the leaf area index, based on the luminance value calculated by the intensity calculation unit as the intensity of light.

3. The leaf area index measurement system according to claim 1, wherein the intensity calculation unit calculates illuminance based on a luminance value of each of the reflectors in the captured images, as the intensity of light, and
wherein the leaf area index calculation unit calculates the leaf area index, based on the illuminance calculated by the intensity calculation unit as the intensity of light.

4. The leaf area index measurement system according to claim 1, further comprising:
a storage unit executed by the processor for storing the leaf area index in association with the intensity of light,
wherein the leaf area index calculation unit calculates the leaf area index by extracting, from the storage unit, the leaf area index corresponding to the intensity of light calculated by the intensity calculation unit.

5. The leaf area index measurement system according to claim 1, wherein the reflectors are provided with a predetermined color, and
wherein the intensity calculation unit specifies, in the captured images, an area in which an object provided with the predetermined color is shown, and calculates an intensity of light of the specified area.

6. A leaf area index measurement device for measuring a leaf area index in a leaf area index measurement system that includes:
a plurality of reflectors placed in a neighborhood of a measurement target plant; and
a processor configured to execute:
an imaging unit placed at a position where no obstacle is present between the imaging unit and the reflectors, and for capturing images of the reflectors and outputting the captured images, the leaf area index measurement device comprising:
the processor configured to execute:
an intensity calculation unit for calculating an intensity of light reflected by each of the reflectors, based on the captured images output from the imaging unit; and
a leaf area index calculation unit for calculating the leaf area index, based on the intensity of light calculated by the intensity calculation unit.

7. A leaf area index measurement method comprising:
providing reflectors in a neighborhood of a measurement target plant;
providing imaging unit implemented by a processor placed at a position where no obstacle is present between the imaging unit and the reflectors, and for capturing images of the reflectors and outputting the captured images;
calculating an intensity of light reflected by each of the reflectors, based on the captured images output from the imaging unit; and
calculating a leaf area index, based on the calculated intensity of light.

8. A non-transitory computer readable information recording medium storing a leaf area index measurement program for measuring a leaf area index in a leaf area index measurement system that includes: a plurality of reflectors placed in a neighborhood of a measurement target plant; and imaging unit placed at a position where no obstacle is present between the imaging unit and the reflectors, and for capturing images of the reflectors and outputting the captured images, the leaf area index measurement program causing a computer to execute:

calculating an intensity of light reflected by the reflectors, based on the captured images output from the imaging unit; and a leaf area index calculation process of calculating the leaf area index, based on the calculated intensity of light.

* * * * *